(12) United States Patent
Peng et al.

(10) Patent No.: US 8,716,656 B2
(45) Date of Patent: May 6, 2014

(54) ION MOBILITY SPECTROMETER AND METHOD FOR IMPROVING THE DETECTION SENSITIVITY THEREOF

(75) Inventors: Hua Peng, Beijing (CN); Zhongxia Zhang, Beijing (CN); Yaoxin Wang, Beijing (CN)

(73) Assignee: Nuctech Company Limited, Beijing (CN)

( * ) Notice: Subject to any disclaimer, the term of this patent is extended or adjusted under 35 U.S.C. 154(b) by 114 days.

(21) Appl. No.: 13/203,078

(22) PCT Filed: Jul. 30, 2010

(86) PCT No.: PCT/CN2010/001151
§ 371 (c)(1),
(2), (4) Date: Aug. 24, 2011

(87) PCT Pub. No.: WO2011/060607
PCT Pub. Date: May 26, 2011

(65) Prior Publication Data
US 2012/0138783 A1  Jun. 7, 2012

(30) Foreign Application Priority Data

Nov. 20, 2009 (CN) .......................... 2009 1 0089161

(51) Int. Cl.
*G01N 33/00* (2006.01)
*H01J 49/00* (2006.01)
*B01D 59/44* (2006.01)
(52) U.S. Cl.
USPC ........... 250/288; 250/282; 250/281; 250/290; 436/173; 436/139; 436/104; 436/120
(58) Field of Classification Search
USPC ............ 250/492.21, 286, 287, 288, 290, 282
See application file for complete search history.

(56) References Cited

U.S. PATENT DOCUMENTS 4,939,103 A * 7/1990 Szolgyemy ................... 438/546
(Continued)

FOREIGN PATENT DOCUMENTS

CN 201417742 Y 3/2010
(Continued)

OTHER PUBLICATIONS

International Search Report in international application No. PCT/CN2010/001151, dated Nov. 11, 2010.

*Primary Examiner* — Nikita Wells
*Assistant Examiner* — Johnnie L Smith
(74) *Attorney, Agent, or Firm* — Marshall, Gerstein & Borun LLP

(57) ABSTRACT

The present invention relates to a method of improving detection sensitivity of an ion mobility spectrometer, comprising: inserting a sample into a sample receiving device of the ion mobility spectrometer; triggering an operation of spectra acquisition through an optocoupler; when the number of the acquired spectra reaches the level required to contain enough information for accurate detection of explosives with relatively high vapor pressure, adding a dopant instantly to the ionization region by controlling the ON/OFF-state of an electromagnetic valve; when the number of the acquired spectra reaches the level required to contain enough information for accurate detection of explosives with relatively low vapor pressure, stopping the acquisition operation, and turning off the electromagnetic valve so as to stop adding the dopant to the ionization region; analyzing all of the acquired spectra to obtain the detection result. The addition time of the dopant is controlled such that the dopant can take effect on the detection of some explosives with relatively low vapor pressure while the explosives which can be detected with higher sensitivity when no dopant is added can be analyzed in the case that the dopant concentration is very low, thereby achieving the optimal detection performance of the apparatus by taking account of its response to various explosives.

10 Claims, 6 Drawing Sheets

(56) References Cited

U.S. PATENT DOCUMENTS

| | | | |
|---|---|---|---|
| 5,032,721 A * | 7/1991 | Bacon et al. | 250/282 |
| 5,234,838 A * | 8/1993 | Bacon, Jr. | 436/173 |
| 5,283,199 A * | 2/1994 | Bacon et al. | 436/173 |
| 5,491,337 A | 2/1996 | Jenkins et al. | |
| 5,962,858 A * | 10/1999 | Gwinn | 250/492.21 |
| 5,968,837 A * | 10/1999 | Doring et al. | 436/173 |
| 6,225,623 B1 * | 5/2001 | Turner et al. | 250/286 |
| 6,495,824 B1 | 12/2002 | Atkinson | |
| 2002/0088936 A1 | 7/2002 | Breach et al. | |
| 2010/0282962 A1 | 11/2010 | Machuron-Mandard et al. | |
| 2011/0297821 A1 * | 12/2011 | Peng et al. | 250/282 |

FOREIGN PATENT DOCUMENTS

| | | |
|---|---|---|
| DE | 19609582 C1 | 5/1997 |
| DE | 10212110 A1 | 9/2003 |
| EP | 0135747 A2 | 4/1985 |
| EP | 0509171 A1 | 10/1992 |
| EP | 1672363 A1 | 6/2006 |
| WO | WO-2004/102611 A2 | 11/2004 |
| WO | WO-2006/123107 A1 | 11/2006 |
| WO | WO-2006/129101 A1 | 12/2006 |
| WO | WO-2007/082941 A1 | 7/2007 |

* cited by examiner

ION MOBILITY SPECTROMETER AND METHOD FOR IMPROVING THE DETECTION SENSITIVITY THEREOF

CROSS-REFERENCE TO RELATED APPLICATIONS

This is the U.S. national phase of International Application No. PCT/CN2010/001151, filed Jul. 30, 2010, which claims the benefit of Chinese Patent Application No. 200910089161.1, filed Nov. 20, 2009.

TECHNICAL FIELD

The present invention relates to an explosives detector and a detection method, particularly relates to an ion mobility spectrometer for the detection of explosives and a method of improving its sensitivity for explosives detection by controlling the addition time of a dopant.

BACKGROUND OF THE INVENTION

The ion mobility spectrometer is a rapid, sensitive and portable apparatus based on ion mobility spectrometry for on-site detection. The apparatus can detect the presence of trace amounts of contrabands, such as explosives, drugs and chemical warfare agents, etc., and has currently found wide applications in the field of security inspection and military affairs.

The core component of the ion mobility spectrometer is an ion drift tube, where ambient air is generally used as the carrier gas. By adopting different sample introduction modes, the collected molecules of the substance to be detected in a gaseous state can be carried into the drift tube by air. In the ionization region of the drift tube, the air molecules are firstly ionized and form reactant ion clusters, then the molecules of substance to be detected interact with the reactant ion clusters to form new molecular ion clusters, i.e., product ion clusters. When the ion gate opens, these molecular ion clusters are injected into the drift region and continue to move forward under the influence of an electric field. In the drift region, the drift velocities of the molecular ion clusters depend on some factors including the mass, charges and spatial structure of the ion clusters so that their arrival times at the detector located at the end of the drift region are different from each other. The substance can be identified by measuring the weak current generated by the collision of the ion clusters onto the detector, determining their corresponding arrival times and matching the values with those recorded in the standard substance library.

The ionization of the gas molecules of the sample to be detected performed in the ionization region of the ion drift tube is a secondary ionization process: the concentration ratio of the carrier gas and the sample vapor causes the carrier gas molecules to be ionized by the ion source more easily than the sample vapor molecules, hence, the ionization process is first performed on the air molecules so as to generate reactant ions. Because the free path for ionized carrier gas molecules is much less than the geometric size of the reaction chamber, the ionized carrier gas molecules and the sample vapor molecules will collide frequently, so that the ion charges are transferred from the ionized carrier gas molecules to the sample molecules. Such transfer reaction between charges is decided by proton or electron affinity of the molecules participated in the reaction, the charges will transfer from molecules with small proton or electron affinity to molecules with large affinity. In actual use of the ion mobility spectrometer, the molecular composition and ionization mechanism of the reactant are generally changed by adding dopants, so as to change the chemical composition of the generated product ions and improve the detection sensitivity and selectivity of the apparatus. The molecules of the dopant must possess electron affinity lower than that of the sample molecules (such as the explosives) while higher than that of other components contained in the carrier gas, hence, it can be ionized first to generate stable ions so as to prevent the disruptors with lower affinity in the carrier gas from participating in the ionization reaction, meanwhile, because the electron affinity of the sample molecules is larger than the reagent molecules, these ions continue to react with the sample vapor molecules to generate sample molecular ions for detection. The adding of the dopant can also enable the spectrogram peak position to which the generated product ions correspond to shift and enable the ion peaks, that are difficult to be identified due to overlapping of peak positions when the dopant is not added previously, to be separated, so as to realize identification of the components to be detected in the case of existence of disruptors.

Currently, there have been many relevant patents that respectively describe the category selection and adding manner of the dopant in the ion mobility spectrometer or other similar analysis apparatus. The early patent such as EP0135747 describes that during detection of samples of drugs and explosives, the acetone and the carbon tetrachloride are added into the carrier gas as dopants before injection of the sample, the generated dimer ion or hydration Cl-ion can prevent inconstant composition cluster phenomenon of water, so that it forms a narrow peak with relatively fixed position on the ion spectrogram, and can be used as the reference point for electric control unit algorithm, so as to enable the apparatus to have better detection and identification specificity.

Relevant patent documents, such as WO2006123107, EP0509171, U.S. Pat. No. 5,283,199, U.S. Pat. No. 5,234,838, U.S. Pat. No. 5,032,721, DE19609582, DE10212110, WO2007085898, have described that the dopants of different categories that can be used in ion mobility spectrometry analysis are applicable for various detection requirements. For example, the use of the dopant containing di-pentanone improves the identification ability to some substances in the gas sample such as nitrogen compounds in the exhaled gas of mammals; adding a small amount of dopant of sulfur dioxide into the sample to be detected through a temperature control and permeable tube can eliminate the interference effect of acid gas components with relatively weak electron affinity such as hydrogen fluoride, sulfur dioxide, mefenamic acid, and improve the selectivity of the apparatus; similarly, using a small amount of substituted phenols (such as methyl salicylate, 2-hydrogen group acetophenone) and amines (such as methylamine) as the dopant can eliminate the interference effect of the chlorine gas; the added dopant dimethyl methylphosphonate (DMMP) can be used with the ammonia gas of the component to be detected to generate cluster ions the drift time of which is changed distinctly, so as to be easily identified from the spectrogram of the mixture gas; the aromatic compounds (benzene, toluene, xylene) added in the sample as the dopants have energy equal or less than that of the VUV ray photons and an ionization potential higher than that of the sample molecules, within the VUV radiation ionization range, it can be used to detect trace substances in the air, it may even detect substances with weak proton affinity only, and can improve the detection sensitivity of electronegative substances; ammonia water can be introduced into the analysis gas so as to separate the reactant ion peak from the formaldehyde peak, and then perform quantitative analysis of the formaldehyde; amides ionization dopants are used to detect peroxide explosives and the like.

On the adding manner of dopants, the patents concerned are PCT patent WO2006129101 and WO2004102611, the apparatus as stated in the former uses at least two reservoirs to provide various dopants, the reservoirs are connected with the ionization chamber of the spectrometer, an inlet is arranged at the side of the selectively permeable membrane facing the sample inlet, so that the sample gas contacts the dopant before the ionization, and the cycle gas circuit in the drift tube is separated from the doping gas circuit; the system described by the latter comprises a molecular sieve with dopants added therein, to which a first kind of dopant can be added successively. The system further comprises additional reservoirs filled with different dopants, other different dopants than the first kind of dopant are added into the air selectively via a switching arrangement. In addition, the apparatus involved in the U.S. Pat. No. 6,495,824 comprises a plurality of reservoirs filled with various dopants. The various dopants are selectively added into the carrier gas stream according to the variation of the detected signal, and react with the sample to generate additive products with different drift rates. An information library can be set up which contains known reaction information of the object to be detected and the various dopants, it can be determined whether the substance to be detected is contained indeed in the sample by comparing the observation result of the sample relative to a specific combination of a variety of dopants with the data in the information library. The patent WO2007082941 injects the object to be detected through the normal ionization interface at the inlet of the apparatus, and adds the additives into the foggy gas. US2002088936 combines the doping gas source with the drying and cleaning apparatus. U.S. Pat. No. 5,491,337 mixes the dopant with low concentration with the carrier gas in a closed container arranged before the sample and air inlet of the apparatus, which is introduced into the ionization chamber together with the sample gas. EP 1672363 mixes the sample gas with the doping gas before the sample gas enters into the apparatus, or adds the doping gas into the drift gas so as to eliminate the interference problem in analysis of the testing sample of a large amount of inert gas by using the ion mobility spectrometer.

In these prior art, the dopants for explosive detection are usually halohydrocarbon class, such as halogenated hydrocarbon. The container for filling dopants needs to have a flow rate control device such as temperature control and semi-permeable membrane, so as to generate sample gas with a specific dopant content and a constant flow rate. The apparatus may comprise two or more containers for filling dopants of different categories, selective adding of dopants of different categories is controlled by arrangements such as electromagnetic valves, so as to improve the ability of the apparatus to correctly identify the object to be detected under the existence of disruptors, or for detection requirements of different objects to be detected.

It is found in actual operations such as security inspection that the dopants has great improving function to the detection sensitivity and selectivity for some importance explosives such as RDX, PSTN, however, the adding of dopants cannot improve the detection capability for all explosives, for some explosives, such as DNT, black powder, relatively high detection sensitivity can be realized in the condition that no dopants exist, the adding of dopants such as chlorinated hydrocarbon molecules on the contrary will greatly reduce the sensitivity. Hence, if the conventional method of providing dopant dosage with a constant concentration by a temperature control and permeable tube is used, it is difficult to realize the optimal detection capability index for said various explosives simultaneously, besides, the preparation and replacement of the temperature control and permeable device increase the complexity and cost of the apparatus.

SUMMARY OF THE INVENTION

With respect to the shortcomings of the above mentioned prior art, the present invention provides an ion mobility spectrometer for detecting explosives and a method of realizing high detection sensitivity of the ion mobility spectrometer for various explosives both before and after the adding of the dopant by controlling the time for adding the dopant.

The ion mobility spectrometer according to the present invention mainly comprises: a sample receiving device, a drift tube, a gas circuit system and a circuit control system. The drift tube is partitioned into an ionization region and a gas drift region by an ion gate, the gas circuit system comprises: a drying gas circuit, a drift gas circuit, a doping gas circuit and a no-load gas circuit, wherein, the drying gas circuit is adapted to provide dried and purified air to the drift gas circuit, the doping gas circuit and the no-load gas circuit respectively;

the drift gas circuit is adapted to introduce the dried and purified air into the gas drift region from the back end of the apparatus as the drift gas flow;

the doping gas circuit is adapted to provide an appropriate amount of dopant vapor and connect with the drying gas circuit based on external control instructions, selectively introducing the dopant vapor carried by the dried and purified air into the ionization region;

the no-load gas circuit is adapted to introduce the dried and purified air into the ionization region.

In the ion mobility spectrometer according to the present invention, the drying gas circuit comprises an air pump for extracting air from the outside and a drying filter for drying and purifying the outside air.

In the ion mobility spectrometer according to the present invention, the doping gas circuit comprises an inlet electromagnetic valve connected with the drying gas circuit and an exit electromagnetic valve connected with the ionization region, a container for filling dopants is arranged between the inlet electromagnetic valve and the exit electromagnetic valve, the inlet electromagnetic valve is a two-position three-way valve, selecting according to an external control instruction, to enable the drying gas circuit to be connected with the doping gas circuit or enable the drying gas circuit to be connected with the no-load gas circuit;

When the content of the external control instruction is ON, the exit electromagnetic valve is turned on, the inlet electromagnetic valve connects the drying gas circuit with the doping gas circuit;

When the content of the external control instruction is OFF, the exit electromagnetic valve is turned off, the inlet electromagnetic valve connects the drying gas circuit with the no-load gas circuit.

The present invention further provides a method of proving detection sensitivity of the ion mobility spectrometer, comprising the steps of:

step one: inserting the sample to be detected into the sample receiving device of the ion mobility spectrometer;

step two: triggering the operation of spectrum acquisition of the ion mobility spectrometer through the sensor arranged at the sample receiving device, the acquired spectra showing the real time information of the weak current representative of the intensity of the ions generated by collision of the ions onto the detector and the arrival time of the ions;

step three: when the number of the acquired spectra reaches the information amount required for accurate detection of explosives with relatively high vapor pressure, adding dopant instantly within the ionization region by controlling the ON-state of an electromagnetic valve;

step four: when the number of the acquired spectra reaches the information amount required for accurate detection of explosives with relatively low vapor pressure, stopping the acquisition operation, and stopping adding dopant to the ionization region by controlling the ON and OFF of the electromagnetic valve;

step five: analyzing all of the acquired spectra based on certain algorithm so as to obtain the detection result.

In step two of the method of improving detection sensitivity of the ion mobility spectrometer according to the present invention, the Optocoupler sensor senses the insertion time of the sample and triggers instantly the operation of spectrum acquisition of the ion mobility spectrometer.

In step two of the method of improving detection sensitivity of the ion mobility spectrometer according to the present invention, the spectrum information is a scanning average value of the real time data representative of the weak current detected by the detector and the arrival time of the ions.

In step two of the method of improving detection sensitivity of the ion mobility spectrometer according to the present invention, the weak current signal is detected by the detector located at the end of the drift tube, the weak current signal is generated by the collision of the molecular ion clusters formed by the molecules of the detected substance onto the current sensor on the detector after being separated by the drift tube under the action of the electrical field, and is representative of the intensity of the molecular ion clusters, the electrical field is generated by the ring electrode slices.

In step three of the method of improving detection sensitivity of the ion mobility spectrometer according to the present invention, the dopant is a solid dopant with small volatilization amount. In the present invention, the dopant is preferably hexachloroethane.

In step three of the method of improving detection sensitivity of the ion mobility spectrometer according to the present invention, the gas circuit that adds the dopant comprises a polytetrafluoroethylene container for filling the dopant, the two ends of which are provided with electromagnetic valves.

In the method of improving detection sensitivity of the ion mobility spectrometer according to the present invention, a drift gas circuit is further comprised, the drift gas circuit is arranged in parallel connection with the doping gas circuit that adds the dopant, when the content of the received external control instruction is OFF, the electromagnetic valve arranged at two ends of the polytetrafluoroethylene container for filling the dopant connects the drying gas circuit with the no-load gas circuit, so that a part of the air dried and purified by the drying gas circuit is used as drift gas added from the tail end of the drift tube, the other part directly enters into the ionization region of the shift tube; when the content of the received external control instruction is ON, the electromagnetic valve arranged at two ends of the polytetrafluoroethylene container for filling the dopant connects the drying gas circuit with the doping gas circuit, so that a part of the air dried and purified by the drying gas circuit passes through the doping gas circuit and carries the dopant to enter into the ionization region of the drift tube.

In the method of improving detection sensitivity of the ion mobility spectrometer according to the present invention, the number of the spectra acquired for analysis every time before turning on the electromagnetic valve that controls adding of the dopant is set in advance.

In step five of the method of improving detection sensitivity of the ion mobility spectrometer according to the present invention, the peak value of the intensity of the ion stream and the corresponding arrival time of the ion shown by the spectra is matched with the standard substance library to determine the category of the detected substance.

The present invention only uses one kind of dopant, by controlling the time for adding the dopant, and based on the difference in gasification speed of various explosives and the influence of the dopant on the actual detection capability thereof, it can be ensured that those explosives with relatively high detection sensitivity in the case of not adding the dopant can be analyzed when the content of the dopants is relatively low, meanwhile, those explosives with relatively high detection sensitivity in the case of adding the dopant can be detected when the doping dosage is adjusted high, thus, the requirement on sensitivity to various explosives during actual detection can be achieved and the selectivity of the apparatus can be increased and the false alert is reduced.

DESCRIPTION OF THE DRAWINGS

FIGS. 5A and 5B are detection result comparison of 50 ngRDX before and after adding of dopants under the same condition in the embodiment of the present invention: wherein, FIG. 5A is a spectrogram before adding the dopants, FIG. 5B is a spectrogram after adding the dopants;

FIGS. 6A and 6B are detection result comparison of 10 ngDNT before and after adding of dopants under the same condition in the embodiment of the present invention: wherein, FIG. 6A is a spectrogram before adding the dopants, FIG. 6B is a spectrogram after adding the dopants;

FIGS. 7A and 7B are schematic diagrams of improving effect on the detection capability of the explosive (50 ngRDX) by controlling the time for adding the dopants in the embodiment of the present invention: wherein FIG. 7A is a schematic diagram of overlapping of ten spectra after sampling without adding the dopants, FIG. 7B is a schematic diagram of overlapping of spectra after sampling by turning on the doping valve instantly by the third spectrum.

FIGS. 8A and 8B are schematic diagrams of improving effect on the detection capability of the explosives (10 ngDNT and 50 ngRDX) by controlling the time for adding the dopants: wherein, FIG. 8A is a schematic diagram of overlapping of ten spectra after sampling of 10 ngDNT without adding the dopants, FIG. 8B is a schematic diagram of overlapping of spectra after sampling of mixture of 10 ngDNT and 50 ngRDX by turning on the doping valve instantly by the third spectrum.

DESCRIPTION OF THE EMBODIMENTS

The method of improving detection sensitivity of the ion mobility spectrometer to explosives, and the specific configuration of the apparatus for implementing the method will be explained in detail as follows with reference to the drawings.

The present invention is based on the insight that improving detection sensitivity of the ion mobility spectrometer to various explosives can be obtained by controlling the time for adding the dopant. When the dopant is added into the ionization region, the charges will be competitively distributed between the dopant molecules and the air molecules, which can be ionized first to generate stable ions, and then react with sample vapor molecules to generate sample molecular ions for detection, so as to prevent the disruptors with lower affinity in the carrier gas from participating in the ionization reaction, so as to improve detection sensitivity and selectivity of the apparatus.

The adding of dopants does not have improving effect to the detection of all explosives, actually, some explosives may have better detection sensitivity when no dopant exists. Hence, the time for adding the dopant during the testing can be controlled by setting the triggering time for adding the dopant, which can achieve detection effect of the apparatus to various explosives, so as to provide an optimal capability index.

Figure 1:
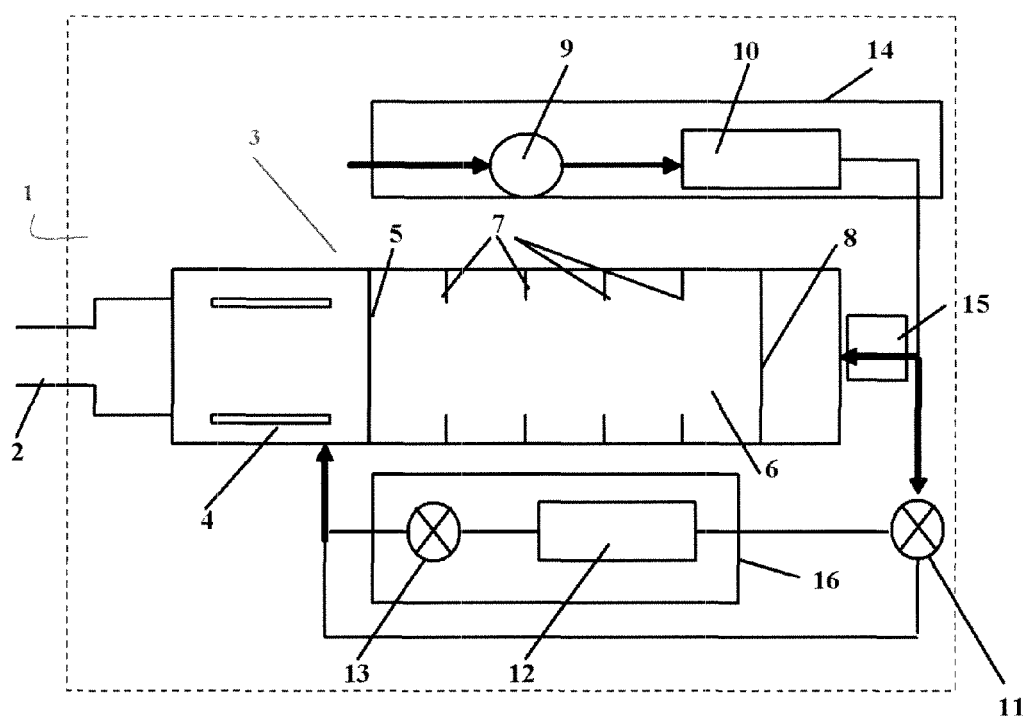
FIG. 1 is a structural schematic diagram of the ion mobility spectrometer applied in the method of according to the present invention.

As shown in FIG. 1, in the method of improving detection sensitivity of the ion mobility spectrometer to explosives according to the present invention, an ion mobility spectrometer 1 used therein comprises a sample receiving device 2, a drift tube 3, and a gas circuit system consisting of a drying gas circuit 14, a drift gas circuit 15, and a doping gas circuit 16.

The drift tube 3 is the core component of the ion mobility spectrometer, it is partitioned into an ionization region 4 and a gas drift region 6 by an ion gate 5. In the gas drift region 6, voltages are applied by ring electrode slices 7 arranged therein to provide a uniformly distributed electrical field, and the acquired substance molecules to be detected enter into the drift tube 3 in a gaseous state together with the air via the sample receiving device 2, in the ionization region 4 of the drift tube 3, the air molecules are ionized to form ion clusters, the explosive molecules interact with these ion clusters to form new molecular ion clusters. When the ion gate 5 is opened, these molecular ion clusters drift forward under the action of the electrical field generated by the ring electrode slices 7, and arrive at a detector 8 at the end of the gas drift region 6. Since different molecular ion clusters arrive at the detector 8 at different times, the category of the detected substance can be determined by detecting the weak current generated by collision of the molecular ion clusters onto the detector and the corresponding arrival time thereof and matching it with the standard substance library.

Now the gas circuit system is further described so as to explain more specifically the working principle of the apparatus of the present invention. As shown in FIG. 1, the drying gas circuit indicated by reference sign 14 comprises an air pump 9 and a drying filter 10. A part of the air abstracted by the air pump 9 from the external environment, after being purified and dried by the drying filter 10, enters into the drift gas circuit indicated by reference sign 15, and is used as drift airflow to enter into the gas drift region 6 from the tail end of the apparatus (drift tube 3), the other part enters into the ionization region 4 at the front part of the apparatus via a further gas circuit connected in parallel with the drift gas circuit 15, the further gas circuit is formed by parallel connection of the doping gas circuit 16 provided with a dopant adding device and the no-load gas circuit (not indicated by reference signs in the drawings) not provided with a dopant adding device. The adding operation of dopants can be controlled by the ON and OFF states of electromagnetic valves 11 and 13 arranged at two ends of a polytetrafluorethylene container 12 for filling dopants in the doping gas circuit 16. Wherein, an inlet electromagnetic valve 11 of the doping gas circuit is, for example, a two-position three-way valve, and is respectively connected with the exit of the drying gas circuit 14 that comprises the drying filter 10 and the inlet of the no-load gas circuit, it connects the drying gas circuit 14 and the doping gas circuit 15 when it is in a first state, and connects the drying gas circuit 14 and the no-load gas circuit when it is in a second state. An exit electromagnetic valve 13 of the doping gas circuit is connected with the gas inlet of the ionization region 4.

When the external control instruction received by the electromagnetic valves 11 and 13 is the first state, the state of the electromagnetic valves 11 and 13 at the two ends of the polytetrafluorethylene container 12 filled with dopants enables the drying gas circuit 14 to be connected with the no-load gas circuit, so that a part of the air dried and purified by the drying gas circuit is used as drift gas added from the tail end of the drift tube 3, meanwhile, the rest part directly enters into the ionization region 4 of the drift tube via the no-load gas circuit. When the content of the external control instruction received by the electromagnetic valves 11 and 13 is the second state, the state of the electromagnetic valves 11 and 13 enables the drying gas circuit 14 to be connected with the doping gas circuit 16, so that part of the air dried and purified by the drying gas circuit passes through the doping gas circuit 16 and carries dopants to enter into the ionization region 4 of the drift tube 3.

The doping gas circuit 16 can provide an appropriate amount of dopant vapor. According to the external control instruction, it connects the drying gas circuit 14, and introduces the dopant vapor into the ionization region 4 through the dried and purified air. In the present invention, the hexachloroethane (solid) for example is used as an exemplary dopant. In one embodiment of the present invention, a small amount of hexachloroethane is filled in the clean polytetrafluorethylene container 12, the covers at the two ends of the container are provided with air-pores, then the container is placed in a stainless steel reservoir, the two ends of which are connected with pipelines, and pass through the electromagnetic valves 11 and 13 to form the doping gas circuit 16 as shown.

The no-load gas circuit configured in parallel with the doping gas circuit 16 is a single pipeline, and is not provided with any extra components specifically, one end of which is connected with the exit of the drying gas circuit 14 that comprises the drying filter 10 via the inlet electromagnetic valve 11, the other end is connected with the gas inlet of the ionization region 4.

According to the above description, the intake of the gas inlet of the ionization region 4 includes two situations: one is that when the exit electromagnetic valve 13 of the doping gas circuit 16 is turned off, and the inlet electromagnetic valve 11 connects the drying gas circuit 14 and the no-load gas circuit, the entered gas is the purified dry air; the other is that when the exit electromagnetic valve 13 of the doping gas circuit 16 is turned on while the inlet electromagnetic valve 11 connects the drying gas circuit 14 and the doping gas circuit 16, the dopant vapor enters into the ionization region 4 carried by the dried and purified air.

On the basis of the above description, it is easy for one skilled in the art to understand that the ion mobility spectrometer according to the present invention further comprises a control circuit that can implement control of the electromagnetic valves 11 and 13, though not shown in the drawings. In addition, the control circuit also controls the operation of real time information acquisition of the detector. And it further comprises an analysis means for analyzing data and performing comparison based on the standard substance library stored in advance. The control circuit and the analysis means can be separated, thereby signal communication will be performed therebetween, optionally, they may also be integrated together. Besides, they can be implemented by hardware, or by a general processor under the operation of programming software, or by combination of hardware and software.

Figure 2:
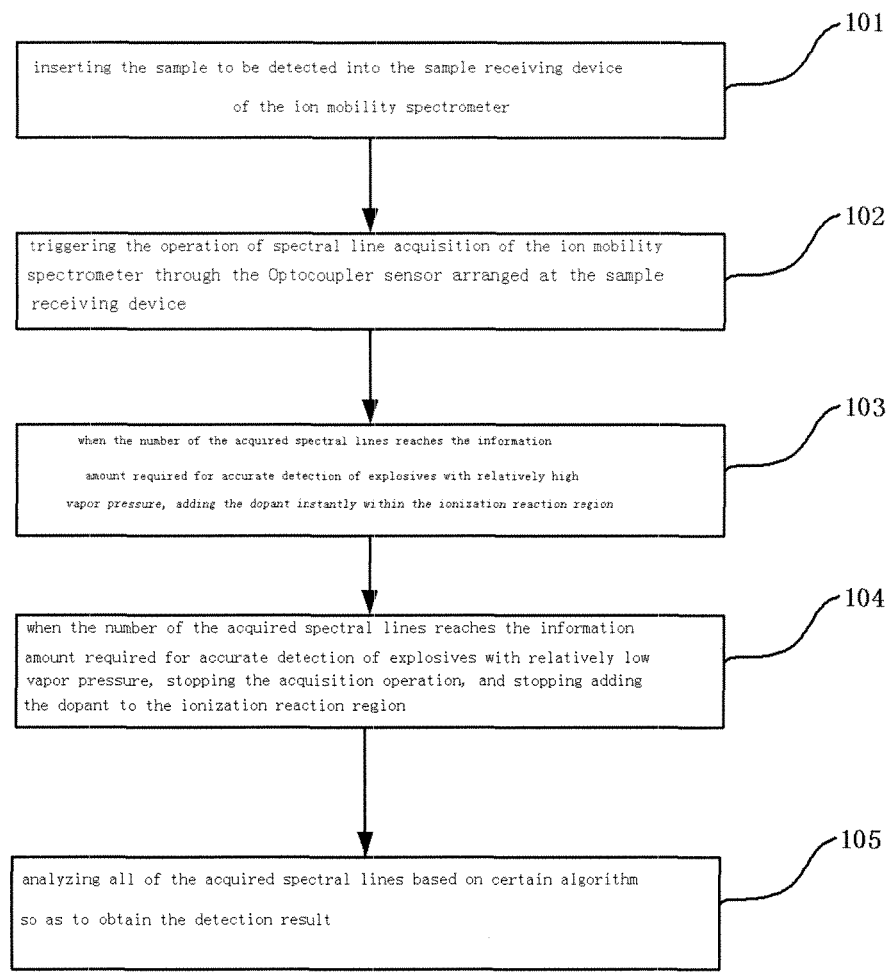
FIG. 2 is a flow chart of the method of improving detection sensitivity of the ion mobility spectrometer according to the present invention.

The method of improving detection sensitivity of the ion mobility spectrometer to explosives is further explained with reference to FIG. 2 in combination with FIG. 1. Specifically, the method comprises the steps of:

Step 101, inserting the sample to be detected such as an object containing explosives into the sample receiving device 2 of the ion mobility spectrometer 1.

In this step, the detected substance is introduced into the drift tube in the form of gaseous molecules after gasification (evaporation) in the sample receiving device of the ion mobility spectrometer.

Step 102, triggering the operation of spectrum acquisition of the ion mobility spectrometer by an Optocoupler sensor arranged at the sample receiving device, the acquired spectra can display real time information, which information represents the weak current generated by collision of the ions onto the detector representative of ion intensity and the arrival time of the ion.

In this step, the air molecules are ionized in the ionization region into reactant ion clusters, and the detected explosive molecules interact with these ion clusters to form new products: molecular ion clusters.

When the ion gate 5 is opened, these molecular ion clusters enter into the drift region under the action of the electrical field formed by the ring electrode slices 7, and continue to drift forward under the action of the electrical field and finally arrive at the detector 8.

It shall be explained that since the drift speed of the molecular ion clusters in the gas drift region is associated with the factors such as the quality thereof, the number of charges it carries, and the spatial structure, the time for different molecular ion clusters to arrive at the detector is different, that is to say, the detector will detect information presented as detectable peak shape that changes with time, which is representative of intensity of ion streams of the detected substance that arrive successively, then the spectra or spectrograms for analysis are obtained after data processing.

Specifically, the spectrogram acquisition and analysis process of the detector can be initiated by the signal of the Optocoupler sensor arranged at the sample receiving device. When the sample is inserted into the sample receiving device, the Optocoupler sensor generates an electrical signal by means of the change of the optical path, so as to trigger the operation of spectrum acquisition of the ion mobility spectrometer instantly when the sample is inserted into the sample receiving device. The acquired spectra are real time information showing the weak current from the detector representative of the ion intensity and the arrival time of the ions. Generally, the actually selected spectrum information is a scanning average value of the real time data representing the weak current detected by the detector and the arrival time of the ion. The weak current signal is detected by the detector at the back end of the drift tube, the weak current signal is generated by collision of the molecular ion clusters formed by the molecules of the detected substance onto the current sensor on the detector after ionized by the drift tube under the action of the electrical field, and representative of the intensity of the molecular ion clusters. The electrical field is generated by the ring electrode slices.

Step 103, when the number of the spectra acquired reaches the information amount required for accurate detection of explosives with relatively high vapor pressure, adding the dopant instantly within the ionization region by controlling the ON-state of the electromagnetic valves.

The gasification of the substance to be detected in the sample receiving device needs a certain period of time, and the gasification speeds of various explosives are not the same, hence, only a certain number (such as 10) of spectra are acquired can sufficient information amount be obtained for detection of existence of various explosive components.

Figure 3:
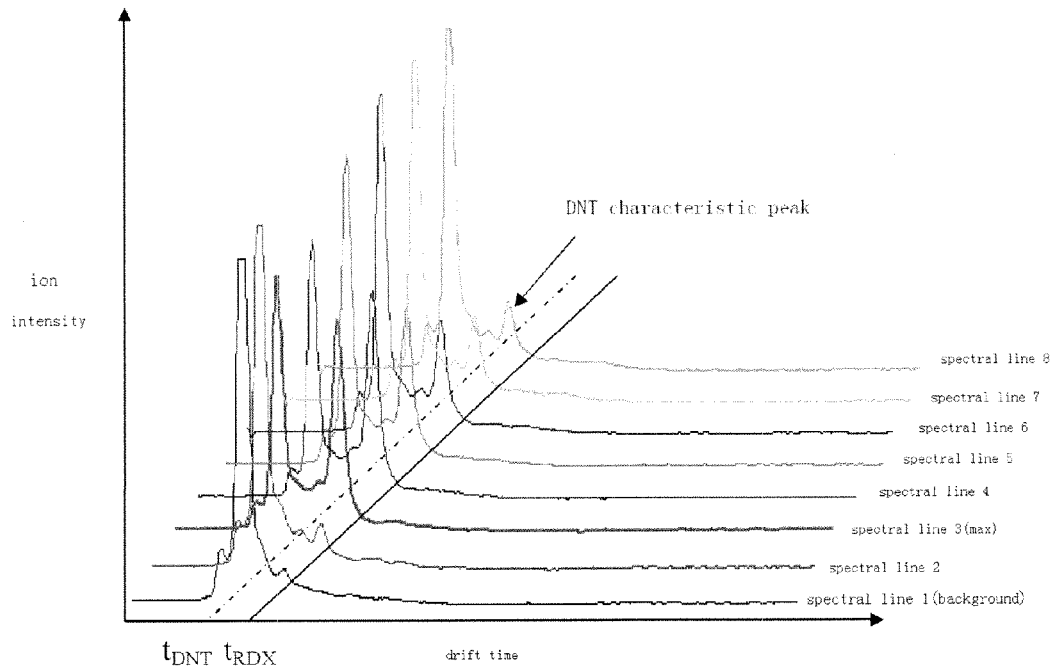
FIG. 3 is a schematic diagram of overlapping of the spectra automatically acquired after sampling of 10 ngDNT in the case of not adding the dopants in the embodiment of the present invention.
Figure 4:
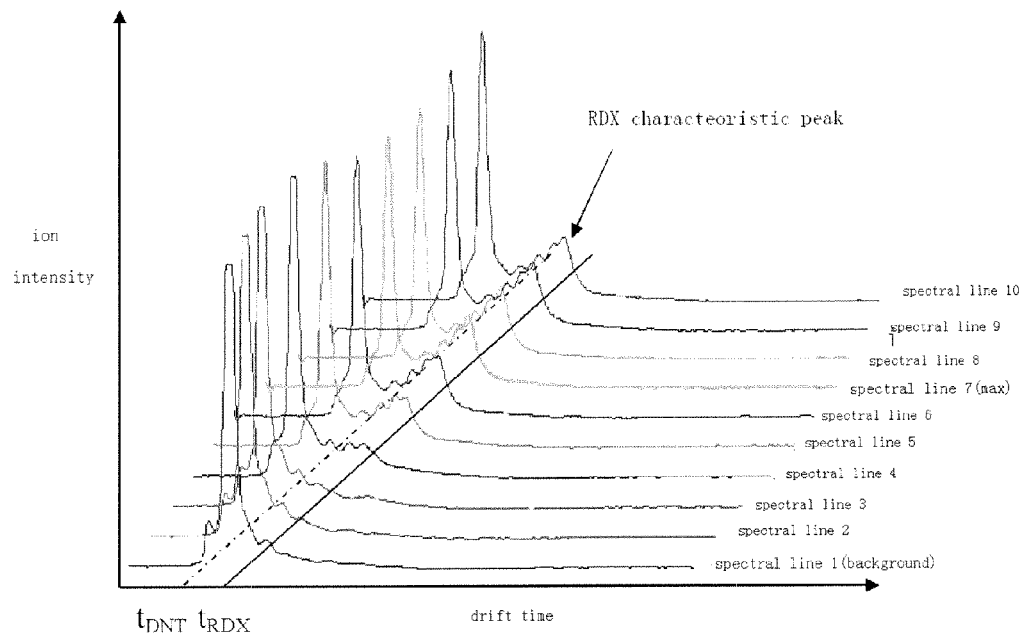
FIG. 4 is a schematic diagram of overlapping of the spectra automatically acquired after sampling of 50 ngRDX in the case of not adding the dopants in the embodiment of the present invention.

Some explosives such as DNT, black powder have relatively high saturation vapor pressures, the gasification speed at the inlet is high, the peak speed is also high; whereas some explosives such as RDX, PETN have relatively low saturation vapor pressures, the gasification speed at the inlet is low, the corresponding peak speed is also relatively low. As shown in FIG. 3 and FIG. 4, the spectrum diagrams successively acquired when testing explosives DNT with relatively high saturation vapor pressure and explosives RDX with relatively low saturation vapor pressure in the case of not adding dopants are respectively shown, which can reflect the difference in peak speed of explosives with different vapor pressures. FIG. 3 shows 8 spectra acquired after sampling of 10 ngDNT, wherein, the substance feature peak appears at the second spectrum, and reaches the maximum peak value at the third spectrum. Hence, after the apparatus initiates the operation of spectrum acquisition, the peak information to which the component to be detected corresponds can be quickly reflected from the spectra that vary in real time, i.e., the several spectra (such as the previous three) initially acquired by the apparatus can contain sufficient information amount for analysis to prove the existence of such explosives. FIG. 4 shows 10 spectra acquired after sampling of 50 ngRDX, wherein, the substance feature peak appears at the fourth spectrum, and reaches the maximum peak value at the seventh spectrum. Hence, after the apparatus initiates the operation of spectrum acquisition, a certain period of time is required to reflect the peak information to which the component to be detected corresponds by observing the spectra that vary in real time, i.e., only the several spectra (such as the subsequent seven) subsequently acquired by the apparatus contain the information that proves the existence of such explosives.

Figure 5A:
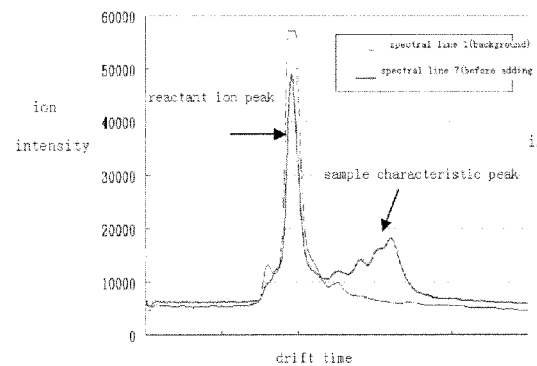
Figure 5B:
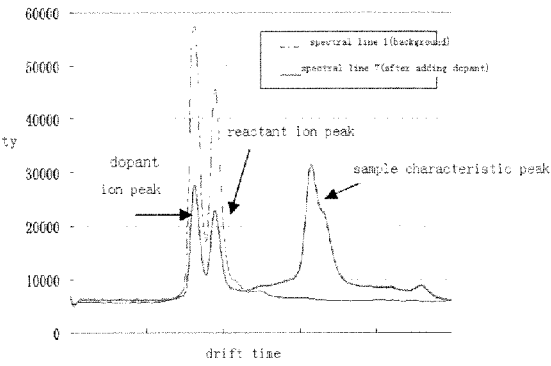
Figure 6A:
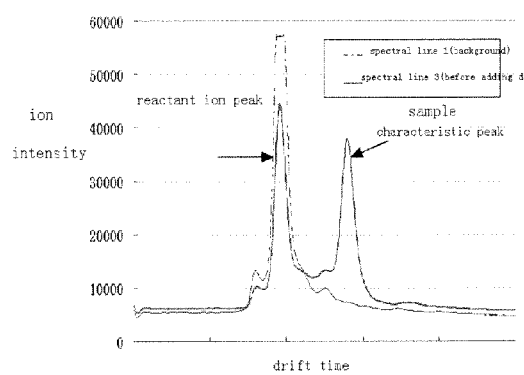
Figure 6B:
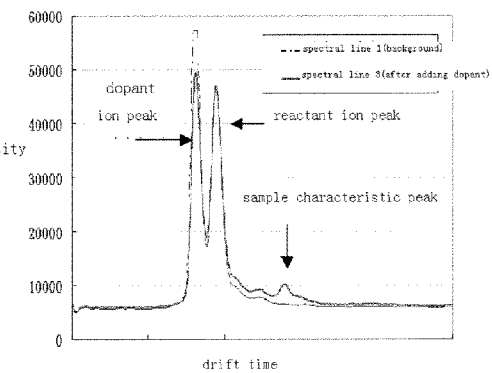

The influence of dopants to detection capability of various explosives can be observed from the comparison of the spectrograms or spectra before and after adding of the dopant when the feature peak of the sample acquired by the apparatus during testing of same amount of explosive samples under the same condition reaches the maximum value. According to actual detection results, although the dopants have great improving effect on the detection sensitivity and selectivity of some important explosives such as RDX, PSTN, some explosives such as DNT, black powder have relatively high detection sensitivity in the case that no dopant exists, the adding of dopants such as chlorinated hydrocarbon molecules will greatly reduce the detection sensitivity of the sample on the contrary. As shown in FIGS. 5A, 5B and 6A, 6B, the comparisons of spectrograms when the feature peak of the sample acquired in testing the explosives RDX and DNT reaches the maximum value in the case of not adding dopants (FIGS. 5A, 6A) and in the case of adding dopants (FIGS. 5B, 6B) are respectively shown. The testing result of 50 ngRDX in FIGS. 5A and 5B shows that the adding of the dopant has obvious improvement on both detection sensitivity and selectivity of the sample, i.e., peak height and peak shape of the sample feature; whereas the testing results of 10 ngDNT in FIGS. 6A and 6B show that the adding of the dopant causes the detection sensitivity of the sample, i.e., peak height of the sample feature, to be distinctly reduced. Hence, if the same amount of dopant is added during the testing process according to the prior art, the optimal detection effect to various explosives cannot be realized actually.

Considering the difference in peak speed of various explosives, the inventor of the present invention recognizes that in the case that no dopant exists, only the previous several spectra are needed for explosives with relatively high detection sensitivity such as DNT, black powder to obtain sufficient information amount for analysis to detect whether the object to be detected exists, whereas in the case of adding the dopant, since the gasification speed of explosives with relatively high detection sensitivity such as RDX, PSTN in the sample receiving device is low, the maximum information amount of the sample cannot be obtained until the subsequent several spectra are acquired, so as to effectively prove whether such explosives exist or not. Hence, different requirements of various explosives to the dosage of the dopant can be realized by controlling the time for adding the dopant.

In the present invention, when initiating the operation of spectrum acquisition initially, for example, under the impel of the Optocoupler sensor signal, the exit electromagnetic valve of the doping gas circuit is in an OFF state, and the drying gas circuit and the no-load gas circuit are connected via the inlet electromagnetic valve, such that in the case of not adding the dopant, spectrum analysis can be performed to those explosives with relatively high detection sensitivity when there is no dopant or the content is very low; whereas when the number of the acquired spectra reaches the information amount required for accurate analysis of the components of explosives such as DNT, black powder with relatively high vapor pressure, for example three spectra, the state of the electromagnetic valve of the doping gas circuit is changed, the exit electromagnetic valve of the doping gas circuit is turned on, and the drying gas circuit and the doping gas circuit are connected via the inlet electromagnetic valve, so as to introduce the dopant vapor into the ionization region. Since the gasification speed of the explosives with relatively high detection sensitivity is low in the case of adding the dopant, these detection signals can be obtained in the state that the dosage of the dopant is adjusted high, such that the requirements for detection sensitivity of various explosives can be considered in actual detection process.

Figure 7A:
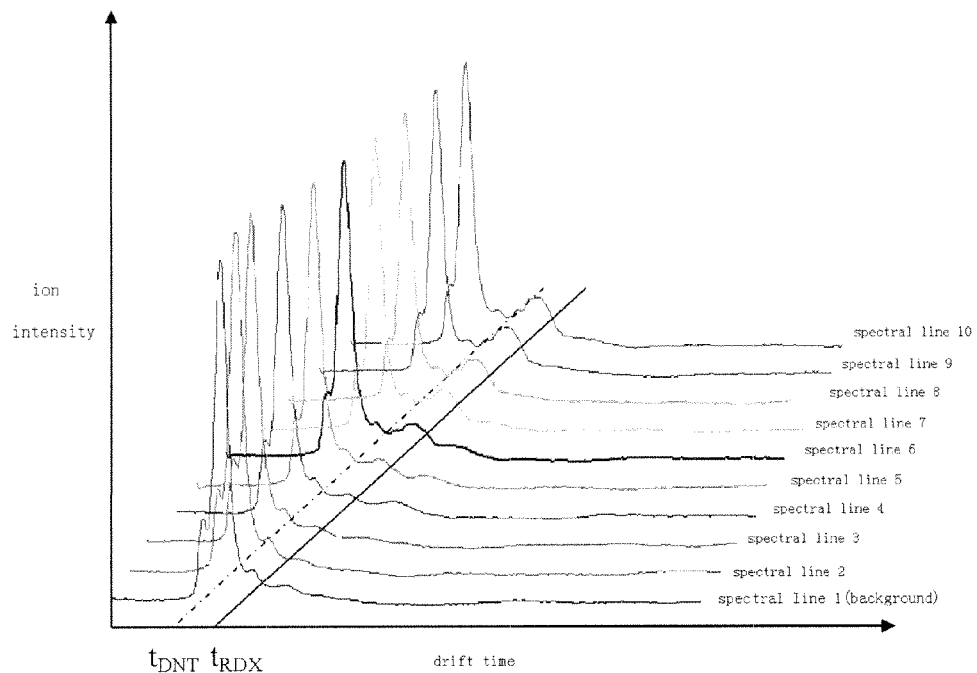
Figure 7B:
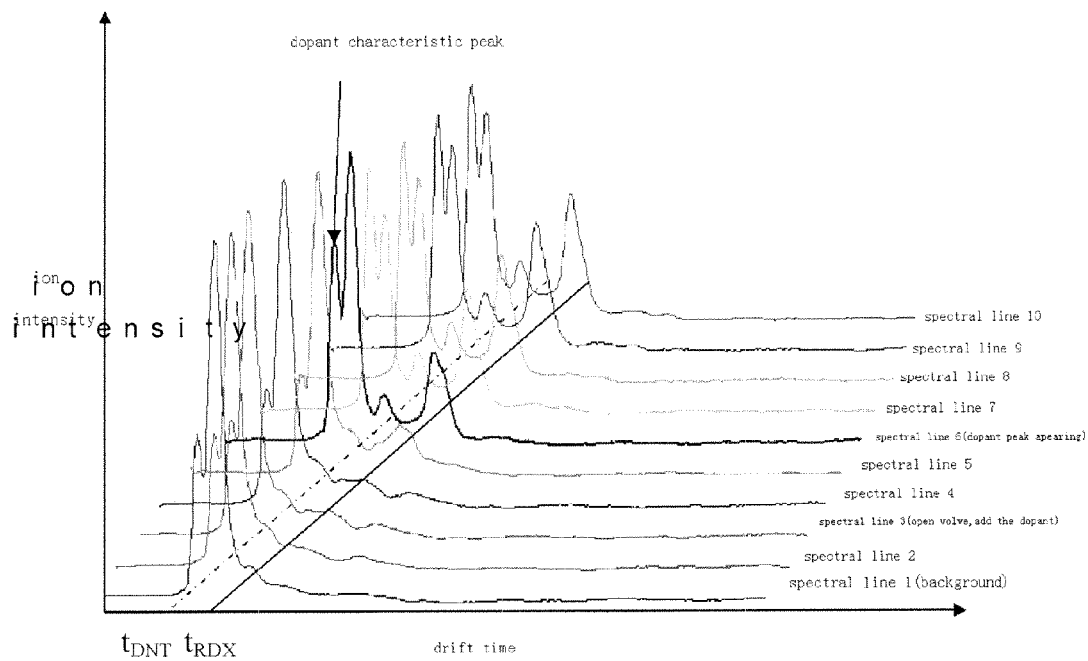
Figure 8A:
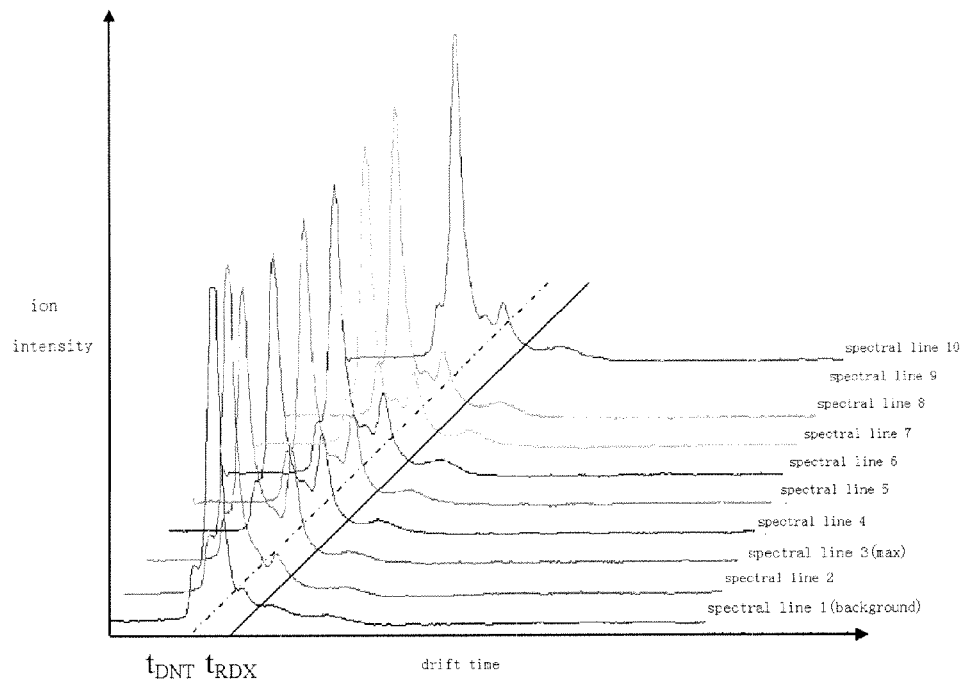
Figure 8B:
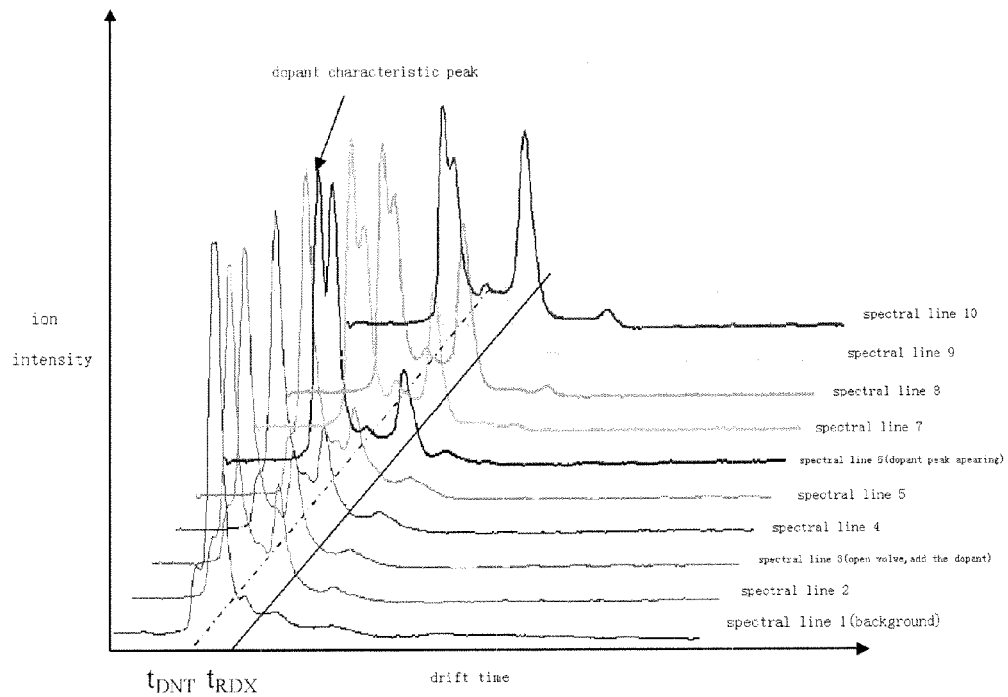

Thus, in this step, when the number of the acquired spectra reaches the information amount for accurate analysis of the components of explosives with relatively high vapor pressures such as DNT, black powder, for example, when the number of the spectra is three, the dopant can be added instantly within the ionization region by controlling the ON-state of the electromagnetic valve. Specifically, the number of the required spectra before changing the state of the electromagnetic valve to control the adding of the dopant each time can be set in advance by a software system arranged inside of the apparatus, and may also be modified according to conditions. As shown in FIG. 7B, when detecting 50 ngRDX, the dopant is added immediately after the spectrum (i.e., the third spectrum) to which the maximum feature peak value of the acquired explosive DNT with relatively high vapor pressure corresponds appears. It can be seen that the dopant feature peak appears distinctly on the sixth spectrum due to hysteresis effect, besides, it can be found from the comparison with the spectra in FIG. 7A that the adding of the dopant has distinct improvement on both the peak height and peak shape of the feature peak of the explosive RDX with relatively low vapor pressure, i.e., the detection sensitivity and selectivity of the sample are greatly improved. Moreover, as shown in FIG. 8B, when the coexisting samples of 10 ngDNT and 50 ngRDX are detected, the dopant is also added instantly at the third spectrum, and the comparison result with FIG. 8A shows that the added dopant does not influence the peak shape and peak height of the feature peak of DNT that form peaks at the previous several spectra at the time of improving distinctly the peak shape and peak height of the feature peak of RDX. It shows that the detection sensitivity of the ion mobility spectrometer to various explosives can be improved by controlling the time for adding the dopant.

The dopant is generally a solid dopant with small volatilization amount. In the present invention, the dopant is preferably solid of hexachloroethane. The gas circuit for adding the dopant comprises the polytetrafluorethylene container for filling the dopant, and the two ends of the container are provided with electromagnetic valves whose operation state can be controlled.

The present invention can further comprise a drift gas circuit connected in parallel with the gas circuit for adding the dopant. The ON and OFF states of the electromagnetic valves are controlled by external instructions. A part of the air dried and purified by the drying gas circuit is used as the drift gas added from the tail end of the drift tube, the rest part directly enters into the ionization region via the no-load gas circuit, or passes through the doping gas circuit and carries the dopant to enter into the ionization region of the drift tube.

In step 104, when the number of the acquired spectra reaches the information amount required for accurate detection the explosives with relatively low vapor pressure, the acquisition operation is stopped, meanwhile, the adding of dopant to the ionization region is stopped by controlling the ON-state of the electromagnetic valve.

In this step, when the number of the acquired spectra reaches the information amount for accurate analysis of various explosives with relatively low vapor pressure, for example, when the number of the spectra is 10, the acquisition operation stops automatically, meanwhile, the exit electromagnetic valve of the doping gas circuit is turned off and the drying gas circuit and the no-load gas circuit are connected via the inlet electromagnetic valve, the adding of dopant to the ionization region is stopped. The number of the spectra to which the above stopping of acquisition operation corresponds can be set in advance by the software system arranged inside the apparatus.

Step 105, performing algorithm analysis to all the acquired spectra to obtain the detection result.

In the present invention, the acquired spectra include the real time information of the weak pulse current detected by the detector and the corresponding arrival time of the ion, which is matched with the standard substance library so as to determine the category of the detected substance.

After one detection is finished, the doping gas circuit needs to be closed, i.e., turning off the exit electromagnetic valve of the doping gas circuit and connecting the drying gas circuit and the no-load gas circuit via the inlet electromagnetic valve, thus, the ion mobility spectrometer can be substantially recovered to the state of low dopant or approximately no dopant within 20 seconds after the end of the spectrum acquisition so as to be prepared for the next detection.

The above detection preparation state of the ion mobility spectrometer can be judged by setting a ratio of the peak height to which the doped ions correspond and the peak height to which the carrier gas molecular ions, i.e., reactant ions correspond. If the apparatus uses the gas sampling mode, the test cannot be performed until the ratio decreases to a certain value, although it will delay the analysis time, it has practical value relative to the benefit brought by improvement on sensitivity. And in actual anti-explosion and security inspection operation, the solid sampling mode is usually used. The sampling process also needs a certain period of time, which will reduce the influence of waiting the recovery of the dosage level of the dopant on the analysis time.

In the method of improving the detection sensitivity of the ion mobility spectrometer to explosives according to the present invention, only one kind of dopant is used, by controlling the time for adding the dopant, and based on the difference in gasification speed of various explosives and the influence of the dopant on the actual detection capability thereof, it can be ensured that those explosives with relatively high detection sensitivity in the case of not adding the dopant can be analyzed when the content of the dopants is relatively low, meanwhile, those explosives with relatively high detection sensitivity in the case of adding the dopant can be detected when the doping dosage is adjusted high, thus, the actual detection sensitivity of various explosives can be achieved and the selectivity of the apparatus can be increased and the false alert is reduced.

It shall be emphasized that the wording "comprise/include" used in the this description is only used to specifically list the existence of the components, steps or elements, however, it does not exclude the existent of other one or more components, steps, elements or the combination thereof.

For one skilled in the art, it is apparent that the respective aspects of the present invention as stated above can be implemented by the software, firmware and hardware in different forms in the embodiments as shown in the drawings. The actual software codes and specific control hardware used for implementing the respective parts in line with the principle of the present invention are not limitations to the present invention. Hence, the description on the operation and capability of the respective parts of the present invention does not make reference to the specific software codes. It is not difficult to understand that any ordinarily skilled person in the out can design the software and control hardware for implementing the respective parts of the present invention according to the description of the present invention.

What is claimed is:

1. An ion mobility spectrometer, comprising:
    a sample receiving device, a drift tube, a gas circuit system, wherein the drift tube is partitioned into an ionization region and a gas drift region by an ion gate, one end of the gas drift region opposite to the ionization region is provided with a detector for detecting ions,
    characterized in that the gas circuit system comprises: a drying gas circuit, a drift gas circuit, a doping gas circuit and a no-load gas circuit, wherein:
    the drying gas circuit provides dried and purified air to the drift gas circuit, the doping gas circuit and the no-load gas circuit respectively;
    the drift gas circuit introduces the dried and purified air as the drift gas flow into the gas drift region from the back end;
    the doping gas circuit provides an appropriate amount of dopant vapor and connects with the drying gas circuit based on external control instructions, selectively introducing the dopant vapor carried by the dried and purified air into the ionization region; and
    the no-load gas circuit introduces the dried and purified air into the ionization region.

2. The ion mobility spectrometer as claimed in claim 1, characterized in that the drift gas circuit is connected in parallel with the gas circuit constituted by parallel connection of the doping gas circuit and the no-load circuit, a part of the dried gas outputted from the drying gas circuit enters into the drift gas circuit, and the other part enters the gas circuit constituted by parallel connection of the doping gas circuit and the no-load gas circuit.

3. The ion mobility spectrometer as claimed in claim 1, characterized in that,
    the doping gas circuit comprises: an inlet electromagnetic valve enabling the doping gas circuit and the drying gas circuit to be selectively connected, an exit electromagnetic valve connected with the ionization region, a dopant container arranged between the inlet electromagnetic valve and the exit electromagnetic valve;
    wherein, the inlet electromagnetic valve is a two-position three-way valve, when it is in a first state, the exit electromagnetic valve is turned on, the inlet electromagnetic value connects the drying gas circuit and the doping gas circuit; when it is in a second state, the exit electromagnetic valve is turned off, the inlet electromagnetic valve connects the drying gas circuit and the no-load gas circuit.

4. An The ion mobility spectrometer as claimed in claim 1, characterized in that the drying gas circuit comprises an air pump for extracting air from the outside and a drying filter for drying and purifying the air.

5. The ion mobility spectrometer as claimed in claim 1, characterized in that it further comprises a control means operable for controlling the ON/OFF operation of the inlet electromagnetic valve and the exit electromagnetic valve.

6. The ion mobility spectrometer as claimed in claim 1, characterized in that the control means is operable for controlling the information acquisition operation of the detector.

7. The ion mobility spectrometer as claimed in claim 1, characterized in that the gas drift region is provided with ring electrode slices for generating a uniform electrical field.

8. The ion mobility spectrometer as claimed in claim 1, characterized in that it further comprises:
    an analysis means comprising a storage unit that stores a standard substance library, for analyzing the information acquired by the detector so as to determine the category of the detected substance.

9. The mobility spectrometer as claimed in claim 1, characterized in that the sample receiving device is provided with an Optocoupler sensor for sensing insertion of the detected object and sending out a corresponding signal.

10. The ion mobility spectrometer as claimed in claim 5, characterized in that the control means is operable for controlling the information acquisition operation of the detector.

* * * * *